United States Patent [19]

Herdle

[11] Patent Number: 4,552,961
[45] Date of Patent: Nov. 12, 1985

[54] PREPARATION OF POLYALKYLENE POLYAMINES USING PHOSPHORUS AMIDE CATALYST

[75] Inventor: William B. Herdle, Greenburgh, N.Y.

[73] Assignee: Union Carbide Corporation, Danbury, Conn.

[21] Appl. No.: 606,000

[22] Filed: May 3, 1984

Related U.S. Application Data

[63] Continuation of Ser. No. 373,725, Apr. 30, 1982, abandoned.

[51] Int. Cl.$^4$ .................. C07D 295/12; C07D 403/12; C07D 403/14; C07C 85/06
[52] U.S. Cl. .................... 544/402; 544/357; 564/478; 564/480; 260/939; 260/959
[58] Field of Search ................ 564/478–480; 544/402, 357; 260/939, 959

[56] References Cited

U.S. PATENT DOCUMENTS

| 3,121,115 | 2/1964 | Meuly | 544/42 |
| 4,036,881 | 7/1977 | Brennan et al. | 564/479 |
| 4,044,053 | 8/1977 | Brennan et al. | 564/479 |
| 4,316,841 | 2/1982 | Ford et al. | 544/402 |
| 4,340,705 | 7/1982 | Lal et al. | 526/141 |

FOREIGN PATENT DOCUMENTS 1500220 2/1978 United Kingdom .

OTHER PUBLICATIONS

Chem. Abstracts; 96:20504c; Bakhitov et al.
Chem. Abstracts; 97:5784w; Palomo et al.

Primary Examiner—Donald G. Daus
Assistant Examiner—William A. Teoli, Jr.
Attorney, Agent, or Firm—Norman L. Balmer

[57] ABSTRACT

Predominantly linearly extended polyalkylene polyamines are produced, in increased conversion rates, by reacting alkylenediamines with alkylene glycols or alkanolamines using a phosphorus amide catalyst in place of phosphorus acid or acid derivative catalysts.

22 Claims, No Drawings

PREPARATION OF POLYALKYLENE POLYAMINES USING PHOSPHORUS AMIDE CATALYST

This application is a continuation of prior U.S. application Ser. No. 373,725, filing date Apr. 30, 1982 now abandoned.

BACKGROUND OF THE INVENTION

1. Field of the Invention

This invention relates to the production of polyalkylene polyamines, and more particularly to the production of predominantly linearly extended polyalkylene polyamines by reacting alkylenediamines with alkylene glycols or alkanolamines using a phosphorus amide catalyst.

2. Description of the Prior Art

The preparation of predominantly non-cyclic, i.e., linear, polyalkylene polyamines is described in U.S. Pat. No. 4,036,881 (Brennan I). The Brennan I patent is one of several patents, including for example U.S. Pat. No. 4,044,053 (Brennan II), involving the production of predominantly noncyclic polyalkylene polyamines using a phosphorus-containing catalyst. The Brennan I patent describes an improved process for reacting alkanolamines with alkylenediamines to selectively produce predominantly noncyclic products. These patents disclose phosphorus-containing catalysts encompassing a wide variety of phosphorus acid or acid derivative compounds. There is no disclosure or indication that phosphorus amide compounds would provide effective alternative catalysts. Instead, the present invention is based on the unexpected discovery that increased conversion rates for polyalkylene polyamine preparation can be achieved through the use of phosphorus amide catalysts in place of the phosphorus-containing substances previously disclosed.

SUMMARY OF THE INVENTION

The present invention relates to a process for producing predominantly linearly extended polyalkylene polyamines comprising:

(a) contacting (i) an alkylenediamine with (ii) a difunctional hydroxy alkylene compound selected from the group consisting of alkylene glycols and alkanolamines; (iii) in the presence of a catalytically effective amount of a phosphorus amide compound; and (b) recovering the polyalkylene polyamines.

The alkylenediamine includes cyclic or non-cyclic alkyleneamine compounds having the structure:

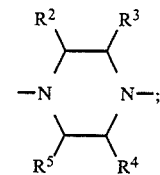

wherein A is

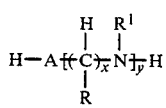

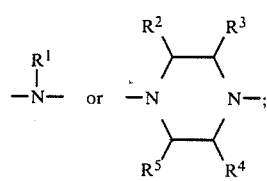

$x$ is an integer greater than 1, preferably from 2 to about 6; $y$ is an integer from 0 to about 6, preferably from 0 to about 2; wherein when $y$ is 0, A is

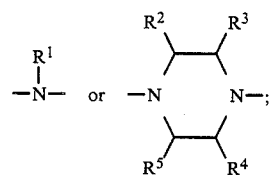

and each of R, $R^1$, $R^2$, $R^3$, $R^4$ and $R^5$ is a hydrogen or lower alkyl, preferably hydrogen.

The difunctional hydroxy alkylene compound includes cyclic or non-cyclic compounds with the structure:

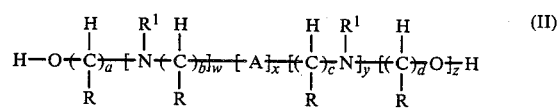

wherein A is

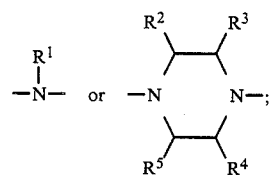

each R, $R^1$, $R^2$ $R^3$, $R^4$, and $R^5$ is hydrogen or lower alkyl, preferably hydrogen; each a, b and c is any integer greater than 1, preferably 2 to about 6; d is 0 or an integer greater than 1; each x and z is 0 or 1; each w annd y is any integer from 0 to about 6, preferably from 0 to about 2; with the provisos that d, w and y are 0 and z is 1 when x is 0; and z is 0 when x is 1 and d is 0.

Phosphorus amide catalysts are compounds which have at least one phosphorus-nitrogen bond, preferably a —P—N—C— or —P—N—H— bond.

This reaction is usually conducted at temperatures of from above about 250° to about 350° C., preferably from 275° to about 325° C.; at a pressure sufficient to provide a reaction mixture in a liquid phase, preferably from about 200 to about 2500 psig; and for a time period sufficient to provide a total reaction conversion of from about 10% to about 80%, usually occurring within from 10 minutes to 20 hours.

DETAILED DESCRIPTION OF THE INVENTION

The present invention provides for an improved process for producing predominantly linearly extended polyalkylene polyamines in enhanced conversion rates by reacting an alkylenediamine with an alkylene glycol or alkanolamine in the presence of a phosphorus amide catalyst.

Reactants

The alkylenediamine reactants are defined as cyclic or non-cyclic compounds, or mixtures of compounds, which contain two primary or secondary, preferably primary, amines separated by alkylene chains. The alkylenediamines which can be generally employed in the present invention include those having the structure:

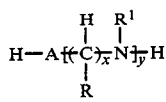 (I)

wherein A is

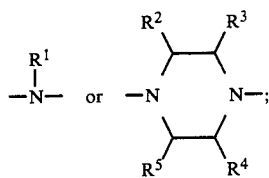

x is an integer greater than 1, preferably from 2 to about 6; y is an integer from 0 to about 6, preferably from 0 to about 2, wherein when y is 0 A is

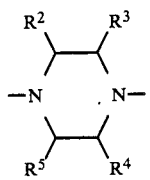

and R, $R^1$, $R^2$, $R^3$, $R^4$ and $R^5$ are hydrogen or lower alkyl, preferably hydrogen.

Some examples of alkylenediamines that can be used as reactants in the process of the present invention, along with their structures defined by the parameters in Formula I, include those listed in Table 1.

TABLE 1

| REPRESENTATIVE ALKYLENEDIAMINE REACTANTS | | | | |
|---|---|---|---|---|
| Alkylenediamine | A | x | y | R | $R^1$ |
| Piperazine | piperazine | — | 0 | — | — |
| N—(2-aminoethyl)-piperazine | piperazine | 2 | 1 | both H | H |
| N—(2-(2-aminoethylamino)-ethyl)-piperazine | piperazine | 2 | 2 | all H | all H |
| Ethylenediamine | amino | 2 | 1 | both H | both H |
| 1,3-Propanediamine | " | 3 | 1 | all H | both H |
| Hexamethylenediamine | " | 6 | 1 | all H | both H |
| Diethylenetriamine | " | 2 | 2 | all H | all H |
| Linear triethylenetetramine | " | 2 | 3 | all H | all H |
| Linear tetraethylenepentamine | " | 2 | 4 | all H | all H |
| N,N'—dimethyl-ethylenediamine | " | 2 | 1 | both H | both $CH_3$ |
| 1,2-Propanediamine | " | 2 | 1 | $CH_3$,H | both H |

Particularly preferred alkylenediamine reactants include ethylenediamine and piperazine. Piperazine is a preferred cyclic reactant for the reason that the process of the present invention provides for the relatively selective attachment of non-cyclic alkyleneamine groups onto the piperazine cyclic ring. In this manner, the cyclic by-products formed during the production of polyalkylene polyamines may be given greater utility by increasing the linear structures within the molecule.

The difunctional hydroxy alkylene reactants are defined as cyclic or non-cyclic compounds, or mixtures of compounds, containing a difunctional alkylene moiety connected at one point to a hydroxy group and at another point, either directly or through a chain of one or more alkyleneamine groups, to another hydroxy group or to an amino group that has at least one hydrogen substituent. The term therefore comprises the classes of alkylene glycols and alkanolamines having active amine hydrogens. Such compounds include those with the structure:

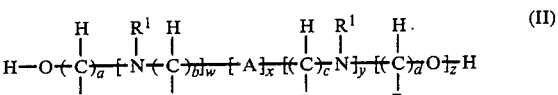 (II)

wherein A is

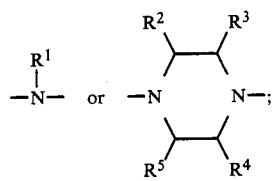

each R, $R^1$, $R^2$, $R^3$, $R^4$, and $R^5$ is hydrogen or lower alkyl, preferably hydrogen; each a, b and c is any integer greater than 1, preferably 2 to about 6; d is 0 or an integer greater than 1; each x and z is 0 or 1; each w and y is any integer from 0 to about 6; preferably from 0 to about 2; provided that d, w and y are 0 and z is 1 when x is 0; and z is 0 when x is 1 and d is 0.

The alkylene glycol reactants include the noncyclic diols of lower alkylene groups. Examples of alkylene glycol compounds are ethylene glycol, propylene glycol, butylene glycol, trimethylene glycol, hexamethylene glycol and the like. A preferred alkylene glycol is ethylene glycol.

The alkanolamine reactants include such compounds as monoethanolamine, diethanolamine, N-(2-aminoethyl)ethanolamine, propanolamines, N,N-bis(hydroxyethyl)piperazine and the like. Preferred alkanolamines include monoethanolamine and diethanolamine.

The R term in the

groups can, of course, represent either hydrogen or various alkyl groups alternatively within the same alkylene chain of x carbon atoms. Similarly, the $R^1$ term in the

groups can, of course, vary between groups.

The relative proportions of alkylenediamine to hydroxy alkylene compound utilized can be from about 6:1 to about 1:1, preferably 3:1 to about 1:1, based on the molar equivalents of amine compound to hydroxy groups. As such, the molar amount of alkylene glycol will usually be about half the molar amount of alkanolamine, used with a given amount of alkylenediamine reactant.

Particularly preferred embodiments of the invention include condensation reactions of ethylenediamine with either monoethanolamine or ethylene glycol.

Catalyst

The phosphorus amide catalyst is a compound having at least one phosphorus-nitrogen, i.e., P—N, bond. Preferably, the P—N bond will be part of a P—N—H or P—N—C-substructure. Compounds containing suitable P—N bonds may have three, four, or five substituents about phosphorus.

Suitable compounds having three substituents about phosphorus may be defined by the formula

(III)

wherein Y is an unsubstituted or alkyl and/or aryl substituted amino radical; R' and R'' are hydroxy, alkoxy, aryloxy, or their thioanalogs, hydrogen, alkyl, aryl, halo, or one of the groups previously defined by Y, and may be joined together with each other or with Y to form a phosphorus-containing heterocyclic ring. If R', R'', or Y contains hydrogen bonded to O, S, or N, such as when R' or R'' is hydroxy or mercapto or Y is monoalkylamino, then corresponding metal salts containing P—O—M, P—S—M, or P—N—M linkages, where M is a monovalent or polyvalent metal or semimetal ion, and anhydrides, thioanhydrides, and condensed phosphorus amides containing respectively P—O—P, P—S—P, and P—N—P linkages may be suitable catalysts as well.

Suitable phosphorus amide catalysts having four substituents about phosphorus include those having the formula,

(IV)

wherein X is an oxygen or sulfur atom, preferably oxygen, and Y, R', and R'' are as defined above. As previously, corresponding metal and semimetal salts and condensed phosphorus compounds may also be suitable.

Suitable phosphorus amide catalysts having five substituents about phosphorus include those having the formula,

(V)

wherein Y is defined as above and R', R'', R''', and R'''' are as defined for R' and R'' above. As previously, corresponding metal and semimetal salts and condensed phosphorus compounds may also be suitable.

Suitable phosphorus amide compounds which can be employed include, for example, the following compounds or their alkyl or aryl derivatives:
phosphoramidous acid, H$_2$N—P(OH)$_2$;
phosphordiamidous acid, (H$_2$N)$_2$POH;
phosphordiamidic acid, (H$_2$N)$_2$P(O)(OH);
phosphoramidic acid, H$_2$NP(O)(OH)$_2$;
alkyl and aryl phosphonamidic acids, RP(O)(OH)NH$_2$;
alkyl and aryl phosphonamidous acids, RP(OH)NH$_2$;
esters and half-esters of the foregoing, e.g. H$_2$NP(OEt)$_2$;
metal salts of the foregoing, e.g. H$_2$NP(O)$_2$K$_2$;
triaminophosphine, (H$_2$N)$_3$P;
triaminophosphine oxide, (H$_2$N)$_3$P(O);
alkyl and aryl phosphonic diamides, RP(O)(NH$_2$)$_2$;
alkyl and aryl phosphonous diamides, RP(NH$_2$)$_2$;
alkyl and aryl phosphinous amides, R$_2$P(NH$_2$);
alkyl and aryl phosphinic amides, R$_2$P(O)(NH$_2$);
analogs of the foregoing substituted with alkyl or aryl groups on nitrogen, e.g. R$_2$NP(OH)$_2$;
and thioanalogs of the foregoing, e.g. R$_2$NP(S)(OEt)$_2$.
The alkyl or aryl substituents on these substances may be linked to phosphorus through more than one atom, so as to form cyclic members of the above classes containing such heterocyclic rings as 1,3,2-diazaphospholidine,

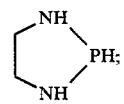

1,3,2-oxazaphospholidine,

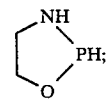

tetrahydro-2H-1,3,2-oxazaphosphorine,

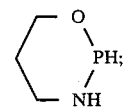

and the like. Such cyclic phosphorus amides may also be used as catalysts in the present invention.

An additional class of phosphorus amides that may be useful as catalysts in the present invention comprises azaphosphoranes in which nitrogen is bound directly to phosphorus. Examples of such compounds include 1,6-dioxa-4,9-diaza-5-phospha(5-P$^V$)spiro[4.4]nonane,

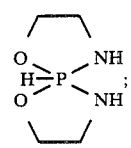

and 2,3,5,6,8,8-hexahydro-8-methyl[1,3,2]oxazaphospholo[2,3-b][1,3,2]oxazaphosphole,

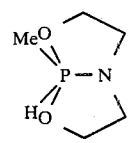

In a preferred embodiment the phosphorus amide catalyst may be formed using the alkylenediamine reactant. This may be accomplished by reacting an excess of the alkylenediamine reactant with phosphoric or phosphorous acid, or derivatives thereof, such as phosphorus trichloride, phosphorus oxychloride, methylphosphonic dichloride, and ethylphosphorodichlorodite. A condensation product of an alkyleneamine with phosphorous or phosphoric acid or a derivative thereof is referred to herein as a phosphorous or phosphoric alkyleneamide. The phosphorus amide catalyst formed in this way may or may not be separated from by-products such as amine hydrochlorides, formed during the catalyst preparation reaction, prior to its use during the condensation reaction. The preparation of the phosphorus amide catalyst may also be carried out in situ by adding a phosphoric or phosphorous acid derivative to the alkylenediamine reactant in the reaction vessel, but prior to the addition of the difunctional hydroxy alkylene reactant. A phosphorus amide catalyst formed from the reaction with the alkylenediamine reactant is preferred since no extraneous alkylamino groups would be introduced into the reaction mixture, where they might react and eventually emerge as contaminants in the desired polyalkylene polyamine products.

Preferred phosphorus amide catalysts include hexamethyl phosphorus triamide, hexaethyl phosphorous triamide and the phosphorus amide reaction product of ethylenediamine with phosphoric or phosphorous acid.

The amount of phosphorus amide catalyst utilized is a catalytically effective amount to cause condensation of the reactants to produce predominantly linearly extended polyalkylene polyamines. This quantity will vary depending upon the reaction conditions and catalyst utilized. Usually a catalytically effective amount will be from about 0.01 to about 10 mole percent, and preferably from about 1 to about 3 mole percent, based on the moles of difunctional hydroxy alkylene compound used.

Reaction Adjuvants and Conditions

The reaction is generally conducted at temperatures of from above about 250° to about 350° C., preferably from about 280° to about 310° C., and most preferably at around 300° C. The reaction is conducted at a pressure sufficient to provide a reaction mixture in a liquid phase, preferably at a pressure of about 200 to about 2500 psig, and most preferably at a pressure of from about 300 to about 700 psig. The reaction is typically conducted for a time period sufficient to provide a total reaction conversion of from about 10% to about 80%, generally within from about ten minutes to twenty hours.

It is preferred that the reaction be conducted without the presence of a solvent; however, the reaction could be conducted using an organic solvent which does not exhibit a deleterious effect upon the reaction.

The process of the present invention may be carried out batchwise or continuously by employing conventional process techniques and apparatus well known to those skilled in the art. In continuous reaction processes, the phosphorus catalysts may be added alone or in combination with the reactants. Alternatively, the catalyst may be provided as a fixed bed on conventional support materials well known to those skilled in the art.

Product

The predominantly linearly extended polyalkylene polyamine product may be recovered using conventional procedures, well established in the art, such as distillation or filtration. The polyalkylene polyamine produced by the process of the present invention is predominantly linearly extended in the sense that the phosphorus amide catalyst provides for the selective formation of linear alkylene chains through polycondensation reactions, minimizing the production of cyclic by-products. When using cyclic reactants containing piperazine substructures, a polyalkylene polyamine product is selectively produced which contains these piperazine groups extended or connected by predominantly linear alkyleneamine units with minimal formation of additional cyclic substructures.

The process of the present invention for reacting alkylenediamines, i.e., compounds containing at least two amine groups containing active hydrogen atoms, with difunctional hydroxy alkylene compounds, i.e., difunctional hydroxy compounds capable of condensing with active hydrogen atoms of amines, provides for a complex series of polycondensation reactions to occur generating a variety of polyalkylene polyamine products.

The preferred predominantly linearly extended polyalkylene polyamines have the structure:

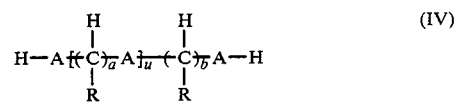

(IV)

wherein R and A are as previously defined; each a and b is any integer greater than 1, preferably from 2 to about 6; and u is an integer from 1 to about 6. Examples of such compounds include:

diethylenetriamine from ethylenediamine and monoethanolamine;

linear triethylenetramine from ethylene glycol and ethylenediamine;

N-(2-aminoethyl)piperazine and N,N'-bis(2-aminoethyl)piperazine from piperazine and monoethanolamine;

N,N'-bis(2-aminoethyl)piperazine and N-(2-(2-aminoethylamino)ethyl)-piperazine from N-(2-aminoethyl)-piperazine and monoethanolamine;

linear tetraethylenepentamine from ethylenediamine and diethanolamine; and linear triethylenetetraamine from ethylenediamine and N-(2-hydroxyethyl)ethylenediamine.

Most preferred compounds are diethylenetriamine, linear tetraethylenepentamine and linear triethylenetetraamine.

In a typical embodiment of the invention, the alkylenediamine is mixed with the difunctional hydroxy alkylene compound and heated in the presence of the phosphorus amide compound at a temperature of from above about 250° to about 350° C., at a pressure sufficient to provide a reaction mixture in a liquid phase, which is usually from about 200 to about 2500 psig. The predominantly linearly extended polyalkylene polyamine can be withdrawn at the end of the batch operation once the desired amount of conversion has been achieved. Alternatively, the reactants may be added continuously to a reaction vessel with the polyalkylene polyamine product separated from a reaction mixture which is continuously withdrawn from the reaction vessel.

The analysis of the polyalkylene polyamines produced by the process of the present invention can be conducted by using standard gas chromatography techniques using columns selected for their ability to separate the individual components that may be present in a particular reaction mixture.

The predominantly linearly extended polyalkylene polyamines are useful in a wide variety of applications, such as chemical intermediates in such areas as the manufacture of chelating agents, fuel additives, corrosion inhibitors, paper wet strength resins, polyamide production, ion exchange resins, epoxy curing agents, asphalt additives, urethane catalysts and pharmaceutical applications.

EXAMPLES

The chemical designations used in the Examples are defined as follows, wherein Me is methyl and Et is ethyl.

| Designation | Description |
| --- | --- |
| AEEA | N—(2-aminoethyl)ethanolamine |
| AEP | N—(2-aminoethyl)piperazine |
| DETA | Diethylenetriamine |
| EDA | Ethylenediamine |
| L-TETA | Linear triethylenetetraamine |
| MEA | Monoethanolamine |
| PIP | Piperazine |
| TEPA | Tetraethylenepentamines (all isomers) |
| TETA | Triethylenetetraamines (all isomers) |

Unless otherwise indicated, all polyalkylene polyamine preparations were conducted in 55–60 mm long and ⅜ inch diameter stainless steel tubular reactors. The experimental procedure, unless otherwise indicated, was conducted as follows. The tube reactor was charged with 1:1 molar ratio of EDA to MEA. The reactor was heated to 300° C., usually in just under 5 minutes, and held at the reaction temperature for about 2 hours. The reaction was then quenched in a water bath, cooling the reactor to room temperature in about 2 to 3 minutes. The polyalkylene polyamine products were analyzed using standard gas chromatography techniques. All identified components are given in weight percent of the recovered liquid product.

EXAMPLE 1

This example set forth a procedure for preparing 1,3-dimethyl-2-ethyl-2-oxo-1,3-diaza-2-phosphacyclopentane,

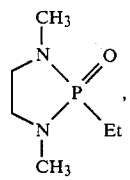

a preferred phosphorus amide catalyst. 3.0 g (34 mmol) N,N'-dimethylethylenediamine, 100 ml of dry toluene, and 6.89 g (68.1 mmol) of triethylamine were placed in an oven-dried, nitrogen-purged flask equipped with a dropping funnel, stirring bar, thermometer, and nitrogen inlet. A solution of 5.00 g (34 mmol) ethylphosphonic dichloride in 10 ml of dry toluene was added dropwise over 25 minutes, keeping the temperature below 45° C. A white precipitate formed as the addition was made. The reaction was stirred overnight under nitrogen at ambient temperature, and then suction-filtered to collect 17.66 grams of solid. The toluene was distilled from the filtrate at one atmosphere, followed by distillation of the residue to produce 3.61 grams of 1,3-dimethyl-2-ethyl-2-oxo-1,3-diaza-2-phosphacyclopentane catalyst.

EXAMPLE 2

Substantially the same procedure in Example 1 was followed using 2.70 grams (30.7 mmol) N,N'-dimethylethylenediamine, and 5.00 grams (30.7 mmol) ethyldichlorophosphate, to produce 1.49 grams of 1,3-dimethyl-2-ethoxy-2-oxo-1,3-diaza-2-phosphacyclopentane,

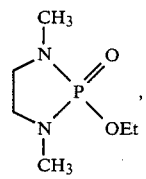

as phosphorus amide catalyst.

EXAMPLE 3

Substantially the same procedure was followed as in Example 1, with 4.00 grams (30.7 mmol) N,N'-diethyl-1,3-diaminopropane and 5.0 grams (30.7 mmol) ethyldichlorophosphate, to produce 1.67 grams of 1,3-diethyl-2-ethoxy-2-oxo-1,3-diaza-2-phosphacyclohexane,

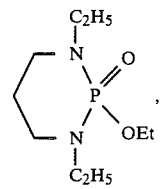

as a phosphorus amide catalyst.

EXAMPLE 4

Substantially the same procedure was followed as in Example 1, with 3.00 grams (34 mmol) N,N'-dimethylethylenediamine and 4.55 grams (31 mmol) ethylphosphorodichloridite to produce 2.31 grams of 1,3-dimethyl-2-ethoxy-1,3-diaza-2-phosphacyclopentane,

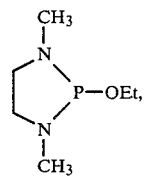

as phosphorus amide catalyst.

EXAMPLE 5

This example demonstrates the preparation of a phosphorus amide catalyst from an alkylenediamine reacted with a phosphorus acid derivative. A solution of 1.00 grams phosphorus oxychloride, POCl₃, in 5 ml toluene was added dropwise to a solution of 3.92 gram ethylenediamine in 20 ml toluene, at a rate such that the reaction temperature remained below 15° C. The mixture was heated at 80° C. for approximately 2 hours, then cooled to room temperature, diluted with 20 ml absolute ethanol, filtered, and the resulting filtrate concentration under a vacuum to a viscous oil containing 3.98% phosphorus and 30.97% nitrogen by elemental analysis.

109 mg of this residue was used to catalyze the reaction between 1.06 grams EDA and 1.05 grams MEA, using the general reaction procedure described above. Gas chromatography analysis indicated a product composition as follows, in weight percent:

| Compound | Weight Percent |
|---|---|
| EDA | 30.3 |
| MEA | 25.2 |
| PIP | 2.7 |
| DETA | 9.9 |
| AEP | 2.5 |
| AEEA | 4.3 |
| TETA | 7.7 |
| TEPA | 2.2 |
| OTHER | 3.0 |

The MEA conversion was determined to be 49.5%.

EXAMPLES 6-16

Examples 6-16 were conducted using substantially the procedures set forth at the beginning of the Example section, to determine the catalytic activity of various phosphorus amide compounds including those produced in Examples 1-4 above. The results are shown in Table 2 below:

TABLE 2

| Example | Catalyst | Catalyst Level[a] | EDA | MEA | PIP | DETA | AEP | AEEA | TETA | TEPA | Others[b] | MEA Conversion[c] |
|---|---|---|---|---|---|---|---|---|---|---|---|---|
| 6 | $(Me_2N)_2PMe$ | .0280 | 32.9 | 16.7 | 2.1 | 16.2 | 2.0 | 2.1 | 7.4 | 5.6 | 2.2 | 65.8 |
| 7 | $(Et_2N)_3PO$ | .0280 | 39.7 | 47.0 | 0.14 | 2.2 | ND | 1.1 | ND | ND | 6.7[e] | 1.0 |
| 8 | $(Me_2N)_3PS$ | .0279 | 43.8 | 45.2 | 0.05 | 0.51 | ND | 0.68 | ND | ND | 2.5[f] | 6.2 |
| 9 | $(Me_2N)_3PO$ | .0280 | 38.9 | 35.1 | ND | 8.2 | 0.3 | —[d] | 2.2 | 0.5 | 3.1[g] | 27.4 |
| 10 | $[(EtO)_2P(O)NHCH_2-]_2$ | .0165 | 27.3 | 15.1 | 1.8 | 17.5 | 1.5 | 2.6 | 8.0 | 2.6 | 5.6 | 68.7 |
| 11 | $[(EtO)_2P(O)NHCH_2-]_2$ | .0140 | 30.0 | 18.1 | 2.8 | 18.6 | 1.2 | 3.2 | 7.2 | 6.0 | 1.9 | 62.7 |
| 12 | (CH3-N piperazine N-CH3 with P(O)OEt) | .0279 | 29.3 | 15.9 | 2.6 | 16.9 | 1.5 | 3.1 | 8.8 | 2.5 | 4.2 | 67.1 |
| 13 | (CH3-N piperazine N-CH3 with POEt) | .0280 | 30.8 | 16.2 | 1.9 | 17.5 | 1.7 | 2.3 | 9.3 | 2.7 | 2.8 | 66.6 |
| 14 | (CH3-N piperazine N-CH3 with P(O)Et) | .0280 | 32.5 | 18.7 | 1.5 | 14.3 | 1.5 | 3.1 | 6.9 | 2.6 | 5.3 | 61.6 |
| 15 | (C2H5-N piperazine N-C2H5 with P(O)OEt) | .0280 | 29.4 | 18.5 | 2.1 | 15.7 | 1.2 | 3.3 | 7.5 | 1.9 | 7.2 | 61.3 |
| 16 | $(Et_2N)_3P$ | .0280 | 26.5 | 13.8 | 1.7 | 18.1 | 1.6 | 2.8 | 9.2 | 3.0 | 2.6 | 71.1 |

[a]Moles per mole MEA.
[b]Weight percent of isolated products, ND = not detected.
[c]Percent of charged MEA consumed, based on assumed 100% mass balance.
[d]Not determined because of interference by $(Me_2N)_3PO$.
[e]Includes 6.6% $(Et_2N)_3PO$.
[f]Includes 2.3% $(Me_2N)_3PS$.
[g]Includes 2.9% $(Me_2N)_3PO$.
[h]Area % in gas chromatogram.

The MEA conversion rate indicate that some phosphorus amide catalysts are more effective than others, such as the noncyclic phosphorus (V) compounds in Examples 7-9.

EXAMPLES 17-28

These examples were conducted to demonstrate the catalytic activity of certain phosphorus amide catalysts while varying reaction conditions, such as temperature, reaction time, and molar ratio of reactants, with the results indicated in Table 3 below:

TABLE 3

| Example | Catalyst | EDA/MEA Molar Ratio | Catalyst Level[a] | Temp. (°C.) | Time (HR) | EDA | MEA | PIP | DETA | AEP | AEEA | TETA | TEPA | OTHERS[n] | MEA Conversion[c] |
|---|---|---|---|---|---|---|---|---|---|---|---|---|---|---|---|
| 17 | (Et₂N)₃PO | 1.00 | 0.0280 | 320 | 2.0 | 41.2 | 40.5 | 0.50 | 4.0 | 0.09 | 1.7 | 0.31 | 0.30 | 7.0[h] | 14.7 |
| 18 | (Et₂N)₃PO | 1.00 | 0.0278 | 320 | 6.0 | 33.1 | 26.6 | 1.0 | 10.5 | 1.0 | 3.1 | 4.3 | 2.5 | 7.0[i] | 44.1 |
| 19 | (Me₂N)₃PO | 1.00 | 0.0280 | 320 | 2.0 | 31.5 | 19.0 | 1.7 | 15.7 | 1.6 | —[g] | 7.7 | 6.0 | 2.9[j] | 60.8 |
| 20 | (Me₂N)₃PO | 1.00 | 0.0280 | 300 | 6.0 | 34.5 | 23.1 | 1.3 | 14.3 | 1.0 | —[g] | 1.5 | 0.30 | 2.8[j] | 29.2 |
| 21 | (Et₂N)₃P | 1.50 | 0.0279 | 300 | 2.0 | 40.4 | 14.2 | 0.98 | 18.3 | 0.89 | 0.94 | 5.7 | 2.4 | 6.0[k] | 63.2 |
| 22 | (Et₂N)₃P[d] | 1.00 | 0.0280 | 300 | 2.0 | 30.4 | 18.8 | 1.6 | 17.0 | 1.5 | 2.7 | 7.4 | 4.9 | 6.3[k] | 60.7 |
| 23 | (Et₂N)₃P[e] | 1.00 | 0.0280 | 300 | 2.0 | 30.2 | 20.2 | 1.4 | 15.7 | 1.4 | 3.4 | 6.5 | 3.8 | 16.6[k] | 57.7 |
| 24 | (Et₂N)₃P[f] | 1.00 | 0.0268 | 300 | 2.0 | 28.7 | 15.9 | 1.6 | 17.4 | 1.6 | 2.3 | 8.0 | 8.0 | 0.62 | 66.7 |
| 25 | (Me₂N)₃PO | 3.00 | 0.0281 | 300 | 2.0 | 64.7 | 19.8 | 0.08 | 4.6 | 0.02 | 0.7 | 0.14 | 0.08 | 1.0[m] | 20.8 |
| 26 | (Me₂N)₃P | 3.00 | 0.0280 | 300 | 2.0 | 56.5 | 7.7 | 0.8 | 16.6 | 0.4 | 0.6 | 3.3 | 0.7 | 0.6 | 69.3 |
| 27 | (Et₂N)₃P | 2.00 | 0.0200 | 300 | 0.5 | 54.3 | 20.4 | 0.5 | 9.6 | 0.23 | 1.5 | 1.5 | 0.2 | 0.34 | 37.7 |
| 28 | (Et₂N)₃P | 2.00 | 0.0200 | 300 | 0.5 | 55.5 | 22.2 | 0.4 | 8.7 | 0.17 | 1.3 | 1.1 | 0.1 | 0.22 | 32.3 |

[a] Moles per mole MEA.
[b] Weight percent of isolated products.
[c] Percent of charged MEA consumed, based on assumed 100% mass balance.
[d] Type 316 stainless steel balls added to tube.
[e] Pyrex glass balls added to tube.
[f] Reactants freeze-thaw degassed and tube sealed under argon.
[g] AEEA not (Me₂N)₃PO.
[h] Includes approximately 5% believed to be Et₂NH.
[k] Includes approximately 5% believed to be Et₂NH.
[m] Includes 1.0% (Me₂N)₃PO.
[n] Area % in gas chromatogram.

EXAMPLES 29–50

These Examples are conducted to determine the comparative effect of a phosphorous amide catalyst, hexaethyl phosphorous triamide, (Et₂N)₃P, with its corresponding hydrolysis product, phosphorus acid, H₃PO₃. The Examples were conducted in part to determine whether the amide could be hydrolyzing under the reaction conditions to produce a catalyst such as a phosphorus acid or acid derivative disclosed in the prior art. The reactions were run were in 75 milliliter reaction vessels, for approximately one half hour, with the results summarized in Table 4 below:

TABLE 4

COMPARISON OF H₃PO₃ WITH (Et₂N)₃P

| Example | Catalyst | Catalyst Level[a] | Charge Size (g)[b] | EDA | MEA | PIP | DETA | AEP |
|---|---|---|---|---|---|---|---|---|
| 29 | H₃PO₃(97%) | .0201 | 50.0 | 58.3 | 23.8 | .46 | 8.4 | .20 |
| 30 | H₃PO₃(97%) | .0200 | 50.0 | 59.5 | 24.6 | .30 | 7.2 | .15 |
| 31 | H₃PO₃(97%) | .0199 | 50.0 | 56.8 | 23.1 | .44 | 9.7 | .16 |
| 32 | H₃PO₃(97%) | .0200 | 50.3 | 57.9 | 24.3 | .34 | 8.4 | .16 |
| 33 | H₃PO₃(97%) | .0200 | 39.9 | 56.8 | 22.6 | .60 | 9.8 | .21 |
| 34 | H₃PO₃(97%) | .0200 | 39.5 | 57.5 | 23.2 | .39 | 9.0 | .16 |
| 35 | H₃PO₃(97%) | .0200 | 25.5 | 57.1 | 22.4 | .41 | 9.9 | .20 |
| 36 | H₃PO₃(97%) | .0200 | 39.9 | 56.8 | 21.6 | .60 | 10.4 | .19 |
| 37 | H₃PO₃(97%) | .0200 | 40.2 | 55.4 | 22.1 | .47 | 10.3 | .19 |
| 38 | H₃PO₃(97%) | .0200 | 40.2 | 56.3 | 23.6 | .49 | 8.7 | .13 |
| 39 | H₃PO₃(97%) | .0200 | 25.4 | 56.5 | 24.4 | .50 | 9.8 | .24 |
| 40 | H₃PO₃(97%) | .0200 | 50.1 | 57.0 | 24.0 | .47 | 9.2 | .17 |
| 41 | H₃PO₃(97%) | .0200 | 26.9 | 57.0 | 22.5 | .41 | 10.1 | .25 |
| 42 | H₃PO₃(97%) | .0200 | 53.8 | 55.8 | 21.4 | .40 | 10.6 | .25 |
| 43 | H₃PO₃(97%) | .0220 | 40.2 | 57.7 | 24.1 | .37 | 8.7 | .14 |
| 44 | H₃PO₃(97%) | .0180 | 40.0 | 57.7 | 23.8 | .38 | 8.9 | .15 |
| 45 | (Et₂N)₃P | .0200 | 42.3 | 55.2 | 21.4 | .65 | 10.8 | .18 |
| 46 | (Et₂N)₃P | .0200 | 41.1 | 54.9 | 21.0 | .67 | 11.3 | .27 |
| 47 | (Et₂N)₃P | .0200 | 50.0 | 56.4 | 23.3 | .27 | 9.1 | .16 |
| 48 | (Et₂N)₃P | .0200 | 51.0 | 53.8 | 20.4 | .48 | 12.0 | .38 |
| 49 | (Et₂N)₃P | .0200 | 56.9 | 54.0 | 20.7 | .46 | 11.3 | .21 |
| 50 | (Et₂N)₃P | .0200 | 47.3 | 52.9 | 18.5 | .62 | 13.3 | .28 |

| Example | AEEA | L-TETA | OTHER TETA | TEPA | OTHERS[g] | Mass Loss(g)[d] | MEA Conversion |
|---|---|---|---|---|---|---|---|
| 29 | 1.0 | 0.58 | .11 | .07 | .18 | −.09 | 28.6 |
| 30 | 0.87 | 0.37 | .08 | ND | .13 | .04 | 26.2 |
| 31 | 1.4 | 0.87 | .21 | .01 | .16 | −.06 | 30.9 |
| 32 | 1.4 | 0.45 | .11 | ND | .14 | −.01 | 27.2 |
| 33 | 1.4 | 0.52 | .21 | ND | .46 | .01 | 32.4 |
| 34 | 1.4 | 0.63 | .12 | ND | .10 | −.01 | 30.4 |
| 35 | 1.5 | 0.86 | .24 | ND | .11 | −.01 | 32.8 |
| 36 | 1.5 | 0.62 | .18 | ND | .46 | −.01 | 35.4 |
| 37 | 1.4 | 1.1 | .30 | ND | .29 | 0 | 33.7 |
| 38 | 1.4 | 0.55 | ND | ND | .27 | 0 | 29.3 |
| 39 | 1.5 | 0.73 | .23 | ND | .29 | −.02 | 27.0 |
| 40 | 1.4 | 0.49 | .37 | .04 | .27 | −.02 | 28.1 |
| 41 | 1.4 | 0.79 | .26 | ND | .11 | −.01 | 32.7 |
| 42 | 1.5 | 0.81 | .22 | ND | .10 | −.01 | 35.9 |

TABLE 4-continued

| | | | COMPARISON OF H$_3$PO$_3$ WITH (Et$_2$N)$_3$P | | | |
|---|---|---|---|---|---|---|
| 43 | 1.5 | 0.44 | .10 | ND | .10 | 0 | 27.7 |
| 44 | 1.6 | 0.69 | ND | ND | .09 | 0 | 28.7 |
| 45 | 1.6 | 0.85 | .44 | ND | .48 | NM | 34.8 |
| 46 | 1.5 | 0.65 | .73 | ND | .49 | NM | 36.2 |
| 47 | 2.4 | 0.74 | .22 | ND | .15 | −.10 | 29.1 |
| 48 | 1.9 | 1.4 | .58 | ND | .17 | .01 | 37.7 |
| 49 | 1.7 | 1.3 | .32 | ND | .15 | .27 | 37.1 |
| 50 | 1.6 | 1.8 | .63 | .03 | .34 | .05 | 43.5 |

$^a$Moles per mole MEA.
$^b$Grams of MEA + EDA charged to cylinder.
$^c$Weight percent of isolated products by gas chromatography with internal standard
$^d$Reactor mass lost during experiment, if any, NM = not measured.
$^e$Percent of charged MEA consumed, based on assumed 100% mass balance.
$^d$Not determined because of interference by (Me$_2$N)$_3$PO.
$^f$Rocked mechanically during reaction time.
$^g$Area % in gas chromatogram.
ND — not detected.

The MEA conversion rate confirms that the catalytic activity of the phosphorus amide catalyst is greater, i.e. provides an overall increase in conversion rates, when compared with the corresponding phosphorus acid catalyst. A statistical analysis of the conversion rates provided an average conversion of 30.8% for the phosphorous acid catalyst as compared with 36.4% for the hexaethyl phosphorous triamide catalyst. These superior results are quite unexpected since there is no indication in the prior art that a particular class of phosphorus compounds would exhibit such enhanced activity, particularly when compared with one of the preferred catalysts of the prior art.

I claim:

1. A process for producing predominantly linearly extended polyalkylene polyamines comprising:
   (a) contacting (i) an alkylenediamine with (ii) a difunctional hydroxy alkylene compound selected from the group consisting of alkylene glycols and alkanolamines; (iii) in the presence of a catalytically effective amount of a phosphorus amide compound having at least one phosphorus-nitrogen bond; and
   (b) recovering the polyalkylene polyamines.

2. The process of claim 1 wherein the alkylenediamine reactant has the structure:

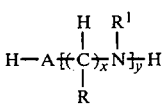

wherein A is

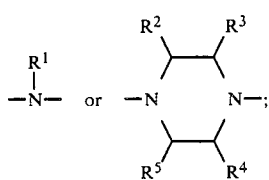

x is an integer greater than 1; y is an integer from 0 to about 6, wherein when y is 0, A is

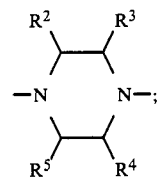

and each R, R$^1$, R$^2$, R$^3$, R$^4$ and R$^5$ is a hydrogen or lower alkyl.

3. The process of claim 1 wherein the difunctional hydroxy alkylene reactant has the structure:

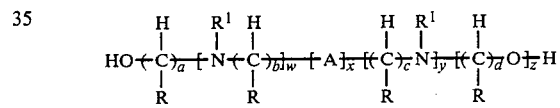

wherein A is

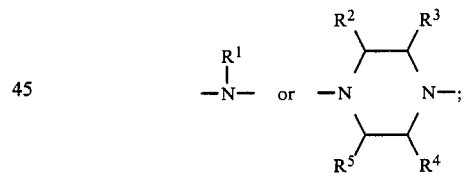

each R, R$^1$, R$^2$ R$^3$, R$^4$, and R$^5$ is hydrogen or lower alkyl; each a, b and c is any integer greater than 1; d is 0 or an integer greater than 1; each x and z is 0 or 1; each w and y is any integer from 0 to about 6; provided that d, w and y are 0 and z is 1 when x is 0; and z is 0 when x is 1 and d is 0.

4. The process of claim 1 wherein the phosphorus amide compound has at least one phosphorus-nitrogen bond.

5. The process of claim 1 wherein the phosphorus amide compound has at least one —P—N—C— or —P—N—H bond.

6. The process of claim 1 wherein the phosphorus amide compound is a phosphoramidous, phosphordiamidous, phosphoramidic, phosphordiamidic, phosphonamidous, or phosphonamidic acid, ester, half-ester, anhydride, or metal salt, a triamino phosphine or triaminophosphine oxide, a phosphonic or phosphonous diamide, a phosphinic amide, or a phosphonic amide.

7. The process of claim 1 wherein the phosphorus amide compound is hexyethyl phosphorous triamide or hexamethyl phosphorous triamide.

8. The process of claim 1 wherein the phosphorus amide compound is a phosphorous or phosphoric alkyleneamide.

9. The process of claim 8 wherein said phosphorous or phosphoric alkyleneamide is formed by reacting phosphorous or phosphoric acid, or a derivative thereof, with the alkyleneamine reactant of step (a) prior to or during the reaction of step (a) but before contacting with the difunctional hydroxy alkylene compound.

10. The process according to claim 8 wherein said phosphorous or phosphoric alkyleneamide is a phosphorus amide of ethylenediamine or diethylenetriamine.

11. The process according to claim 1 wherein the phosphorus amide compound contains a phosphorus atom having an oxidation level of three.

12. The process of claim 1 wherein the reaction is conducted at temperatures of from above about 250° to about 350° C., at a pressure sufficient to provide a reaction mixture in a liquid phase, for a time period sufficient to provide a total reaction conversion of from about 10% to about 80%.

13. The process of claim 12 wherein said temperature is from about 275° C., said pressure is from about 200 to 2500 psig, and said time period is from 10 minutes to 20 hours.

14. The process of claim 1 wherein the relative proportion of alkylenediamine to difunctional hydroxy alkylene compound in mole equivalents is from about 6:1 to about 1:1.

15. The process of claim 14 wherein the relative proportion of alkylenediamine to difunctional hydroxy alkylene compound is from about 3:1 to 1:1.

16. The process of claim 2 wherein the alkylenediamine has a structure wherein x is from 2 to about 6; y is from 0 to about 2; and all R groups are hydrogen.

17. The process of claim 16 wherein the alkylenediamine is ethylenediamine or piperazine.

18. The process of claim 3 wherein the difunctional hydroxy alkylene compound has a structure wherein a is from 2 to about 6; w is from 0 to about 2; y is 0; and all R groups are hydrogen.

19. The process of claim 17 or 18 wherein the hydroxy containing compound is ethylene glycol, monoethanolamine or diethanolamine.

20. A process for producing predominantly linearly extended polyalkylene polyamines comprising reacting an alkylenediamine with a difunctional hydroxy alkylene compound selected from the group consisting of alkylene glycols or alkanolamines, wherein the improvement comprises providing a phosphorus amide catalyst having at least one phosphorus-nitrogen bond.

21. A process for producing predominantly linearly extended polyalkylene polyamines consisting essentially of:
(a) contacting (i) an alkylenediamine with (ii) a difunctional hydroxy lower alkylene compound selected from the group consisting of alkylene glycols and alkanolamines; (iii) in the presence of a catalytically effective amount of a phosphorus amide compound having at least one phosphorus-nitrogen bond, said phosphorus amide compound being formed prior to being contacted with said difunctional hydroxy lower alkylene compound; and
(b) recovering the polyalkylene polyamines.

22. The process of claim 21 wherein the alkylenediamine reactant has the structure:

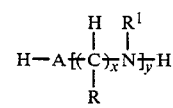

wherein A is

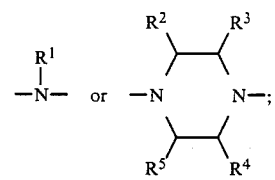

x is an integer from 2 to about 6; y is an integer from 0 to about 6, wherein when Y is 0, A is

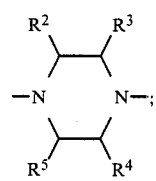

and each R, $R^1$, $R^2$, $R^3$, $R^4$ and $R^5$ is a hydrogen or lower alkyl.

* * * * *

UNITED STATES PATENT AND TRADEMARK OFFICE
CERTIFICATE OF CORRECTION

PATENT NO. : 4,552,961
DATED : November 12, 1985
INVENTOR(S) : William Bruce Herdle It is certified that error appears in the above—identified patent and that said Letters Patent is hereby corrected as shown below:

Column 6, line 3, "RP(O)(NH)$_2$;" should be -- RP(O)(NH$_2$)$_2$;--.

Table 3, footnote g "AEEA not (Me$_2$N)$_3$PO" should be -- g AEEA not determined because of interference by (Me$_2$N)$_3$PO --.

Column 13, lines 25, 26 and 27 the following was omitted

--h Includes 6.4% (E+$_2$N)$_3$ PO --.

-- i Includes 5.4% (E+$_2$N)$_3$ PO --.

-- j Includes 2-2.3% (Me$_2$N)$_3$PO --.

Column 17, line 27 "after 275°C" insert -- to about 325°C, --.

Signed and Sealed this

Ninth Day of December, 1986

*Attest:*

DONALD J. QUIGG

*Attesting Officer*  *Commissioner of Patents and Trademarks*